(12) United States Patent
Cotter et al.

(10) Patent No.: US 9,398,776 B2
(45) Date of Patent: *Jul. 26, 2016

(54) NUTRITIONAL SUPPLEMENTS FOR 50+ INDIVIDUALS FOR IMPROVING VITALITY, IMMUNITY, EYE AND BONE HEALTH

(75) Inventors: Richard Cotter, Mendham, NJ (US); Charles Mohs, Morristown, NJ (US); Lisa Dispensa, Airmont, NY (US); Paula Ziegler, Madison, NJ (US)

(73) Assignee: Wyeth LLC, New York, NY (US)

( * ) Notice: Subject to any disclaimer, the term of this patent is extended or adjusted under 35 U.S.C. 154(b) by 64 days.

This patent is subject to a terminal disclaimer.

(21) Appl. No.: 13/145,684

(22) PCT Filed: Jan. 21, 2010

(86) PCT No.: PCT/US2010/021601
§ 371 (c)(1),
(2), (4) Date: Jul. 21, 2011

(87) PCT Pub. No.: WO2010/085535
PCT Pub. Date: Jul. 29, 2010

(65) Prior Publication Data
US 2011/0280955 A1 Nov. 17, 2011

Related U.S. Application Data

(60) Provisional application No. 61/146,695, filed on Jan. 23, 2009.

(51) Int. Cl.
| | | |
|---|---|---|
| A23L 1/29 | (2006.01) |
| A23L 1/30 | (2006.01) |
| A61K 31/07 | (2006.01) |
| A61K 31/122 | (2006.01) |
| A61K 31/355 | (2006.01) |
| A61K 31/375 | (2006.01) |
| A61K 31/51 | (2006.01) |
| A61K 31/525 | (2006.01) |
| A61K 31/59 | (2006.01) |
| A23L 1/302 | (2006.01) |
| A23L 1/304 | (2006.01) |

(52) U.S. Cl.
CPC ............... *A23L 1/296* (2013.01); *A23L 1/302* (2013.01); *A23L 1/304* (2013.01); *A61K 31/07* (2013.01); *A61K 31/122* (2013.01); *A61K 31/355* (2013.01); *A61K 31/375* (2013.01); *A61K 31/51* (2013.01); *A61K 31/525* (2013.01); *A61K 31/59* (2013.01)

(58) Field of Classification Search
CPC ............ A23V 2250/156; A23V 2250/70; A23V 2250/16; A23V 2250/161; A23V 2250/1612; A23V 2250/704; A23V 2250/1578; A23V 2250/1588; A23V 2250/1642; A23V 2250/702; A23V 2250/708; A23V 2250/712

See application file for complete search history.

(56) References Cited

U.S. PATENT DOCUMENTS

| | | | | |
|---|---|---|---|---|
| 6,475,510 B1 * | 11/2002 | Venkatesh | ............ | A61K 9/0056 424/441 |
| 2003/0190369 A1 | 10/2003 | Lovett | | |
| 2005/0214383 A1* | 9/2005 | Bubnis et al. | ................. | 424/641 |
| 2005/0281889 A1 | 12/2005 | Chandra | | |

FOREIGN PATENT DOCUMENTS

| | | |
|---|---|---|
| BE | 1 016 566 A4 | 2/2007 |
| JP | 2006 131611 A | 5/2006 |
| KR | 20080095276 | 1/2008 |
| KR | 20080008155 | 10/2008 |
| WO | WO 02/052954 A2 | 7/2002 |

OTHER PUBLICATIONS

Marra et al, American Journal of Public Health, Jul. 2008, vol. 98, pp. 1171-1176.*
Salzman et al. (Journal of Pediatric Hematology/Oncology, 2002, vol. 24, pp. 582-584; abstract).*
Zhang et al. Journal of Agricultural and Food Chemistry, 2014, vol. 62, pp. 6687-6698).*
Gonzalez-Molina et al (Journal of Pharmaceutical and Biomedical Analysis, 2010, vol. 51, pp. 327-345).*
Cabrera et al (Meat Science, 2014, vol. 98, pp. 435-444).*
"Patient Information Leaflet Forceval Capsules" Alliance Pharmaceuticals Avonbridge House, Bath Road, Chippenham, Wiltshire, SN15 2BB May 23, 2008.
Databases Biosis Biosciences Information Service, Philadelphia, PA, Importance of Calcium, Vitamin D and Vitamin K for Osteoporosis Prevention and Treatment, May 2008, 67(2):163-76.
PCT Notification Concerning Transmittal of International Preliminary Report on Patentability; mailing date Aug. 4, 2011.
Registr lekarstrvennyh sredstv Rossii. Encyclopedia lekarstv, M: "RLS-2008", 2007, pp. 317, 969 and 970 and the English translation of the relevant parts.
Ratsional'noe pitanie. Normy fisiologicheskih potrebnostey dlya razlichnyh grupp naseleniya Rossiyskoy Federatsii. MR 2.3.1.2432-08, pp. 16 to 25 and the English translation of the relevant parts, 2008.
Tutel'an V.A. et al. Biologicheski activnye dobavki v pitanii cheloveka, Tomsk: Izdatelstvo NLT, 1999, p. 181 and the English translation of the relevant parts.

* cited by examiner

*Primary Examiner* — Sean Basquill
*Assistant Examiner* — Mark V Stevens
(74) *Attorney, Agent, or Firm* — Jeffrey M. Gold; Maureen P. O'Brien; Paula K. Davis

(57) ABSTRACT

A nutritional supplement for adults fifty years and older, and methods of use thereof, are provided that are designed to be most effective in optimizing health, improving vitality and immunity, and improving, aiding, eye and bone health.

1 Claim, No Drawings

NUTRITIONAL SUPPLEMENTS FOR 50+ INDIVIDUALS FOR IMPROVING VITALITY, IMMUNITY, EYE AND BONE HEALTH

BACKGROUND OF THE INVENTION

Nutritional deficiencies occurring in adults are many and vary according to geographic setting and socioeconomic status of the individual. Adults over 50 years of age are at risk of undernutrition (defined as hyponutrition or deficient nutrition) due to physical, cognitive or functional decline. Nutritionists speculate that depression, memory loss, and debility in some cases may result from undernutrition. Chronic diseases such as Alzheimer's, arthritis, or osteoporosis can also interfere with meal preparation and eating habits. Often times, adults over 50 physically are unable to prepare their own meals and then choose to skip the meal altogether.

Even when health status is not a factor, adults over 50 living alone may not bother preparing balanced and nutritious meals for themselves. As an alternative, many may subsist instead on processed, ready-to-eat foods. Economic restraints also affect food choice and nutrient intake. Many adults 50 years and older are on a limited income and therefore, economic considerations as well as lack of nutrition knowledge and health education among adults 50 years and older compounds the problem. Inactivity or illness can further depress the appetite, as can a loss of taste; older people who eat alone or who are depressed can also lose interest in food. Appetite loss may also be caused by dental problems (including poorly fitting dentures, poor dentition, and gum disease), lack of exercise or a diminished sense of smell and taste.

Even adults over 50 who are in perfect health without any disease or other complicating factors cited above can suffer from nutritional deficiencies due to physiological changes that effect the absorption of vitamins, minerals and other macro- and micronutrients. The greatest change in gastrointestinal physiology affecting nutrient bioavailability that has been identified with advancing age is atrophic gastritis, which occurs in a considerable percentage of the adults over 50.

Dietary manipulation is useful to enhance the needed intestinal absorption with ageing populations. Although nutritional supplements for adults over 50 are commercially available, the amounts of nutrients contained in the supplements are generally arbitrary and lack a scientific or experimental basis. Vitamin and mineral preparations are commonly administered as general nutritional supplements, focused upon "completeness" providing one of each vitamin and/or mineral and are not specifically formulated to address specific dietary and nutritional needs based upon individual lifestyles, particularly in a population over 50 years of age.

Micronutrients are elements or compounds which are present in foods in small or trace amounts and includes vitamins, minerals, or other elements and compounds found in foods for which many have not yet qualified for a recommended daily allowance (RDA). The macronutrients consist of carbohydrates, fats, and proteins that supply nutrients and calories and mostly are consumed via food and dietary intake. Some micronutrients such as calcium, sodium, potassium, chloride, and phosphorus are consumed in relatively large amounts, while many others such as iron, iodine, and zinc are consumed in small amounts. Vitamins, such as B12 and folic acid, and minerals such as selenium, are consumed in very small or trace amounts. In as much as the human body does not synthesize many compounds which are essential to the human body, these specific vitamins and minerals can be obtained from only two sources: food and supplements.

The primary source of all nutrients is food. However, the majority of adults over 50 however do not meet the RDA of essential micronutrients through food consumption. Thus, vitamin and mineral supplementation has become a recognized method of meeting accepted medical and health standards.

In an effort to combat these sub-optimal vitamin levels, there have been a variety of nutritional supplements made available to the public. Very typically, these vitamin and mineral supplement formulations are developed so that each dietary ingredient is at one hundred percent (100%) of the RDA without any focus upon key ingredients or supplementation to deliver specific consumer benefits, particularly taking into account physiological factors as people age.

In the alternative, some people and vitamin products take nutritional supplementation to the extreme through megadose vitamin therapy. Megadose vitamin therapy is the use of vitamins in amounts considerably greater than the RDA, often at excessive levels of 200%, 300% etc. However, megadoses of vitamins and/or minerals can have harmful effects, especially in a population who is over 50 years of age. It is appreciated by those skilled in the art that administration of very large doses of certain vitamins, for example vitamins A, C, D and B6 can lead to vitamin toxicity and other serious health consequences. Vitamin toxicity is a condition in which a person develops symptoms as side effects from taking massive doses of vitamins. Vitamin toxicity, which is also called hypervitaminosis or vitamin poisoning, is becoming more common in developed countries because of the popularity of vitamin supplements. Vitamins vary in the amounts that are required to cause toxicity and in the specific symptoms that result.

Therefore, the inventors wanted to provide formulations that are specifically formulated to improve and/or enhance vitality, immunity, eye and bone health, while addressing vitamin and nutrient deficiencies as well as physiological changes in adults over 50 years of age without the negative side effects of a megadose nutritional supplement. The nutritional supplements of the present invention are balanced formulas that address specific indications without using megadose vitamin therapy.

Therefore, there exists a need for a nutritional supplement for adults over 50 years of age that supplies the right amount of the right micronutrients to assure adequate intake needed for disease prevention and protection against nutritional losses and deficiencies due to lifestyle, age, disease and inadequate dietary patterns.

SUMMARY OF THE INVENTION

In one aspect of the invention is provided a nutritional supplement for providing nutritional support for improved vitality, improved immunity, eye and bone health in a human subject fifty years of age and older comprising: an effective amount of vitamin A; an effective amount of vitamin B1; an effective amount of vitamin B2; an effective amount of niacin; an effective amount of vitamin B6; an effective amount of vitamin B12; an effective amount of vitamin C; an effective amount of vitamin D; an effective amount of vitamin E; an effective amount of vitamin K; an effective amount of biotin; an effective amount of folic acid; an effective amount of pantothenic acid; an effective amount of calcium; an effective amount of chloride; an effective amount of chromium; an effective amount of copper; an effective amount of iodine; an effective amount of iron; an effective amount of magnesium; an effective amount of manganese; an effective amount of molybdenum; an effective amount of phosphorus; an effective amount of potassium; an effective amount of selenium; and an effective amount of zinc; wherein the vitality, immunity, eye and bone health is supported.

In yet another aspect of the invention is provided a nutritional supplement for providing nutritional support for improved vitality, improved immunity, eye and bone health in a human subject fifty years of age and older comprising: vitamin A in an amount of about 800 mcg; vitamin B1 in an amount of about 1.4 mg; vitamin B2 in an amount of about 1.75 mg; niacin in an amount of about 20 mg; vitamin B6 in an amount of about 2 mg; vitamin B12 in an amount of about 2.5 mcg; vitamin C in an amount of about 100 mg; vitamin D in an amount of about 5 mcg; vitamin E in an amount of about 15 mg; vitamin K in an amount of about 30 mcg; biotin in an amount of about 62.5 mcg; folic acid in an amount of about 200 mcg; pantothenic acid in an amount of about 7.5 mg; calcium in an amount of about 162 mg; chloride in an amount of about 36.3 mg; chromium in an amount of about 40 mcg; copper in an amount of about 0.5 mg; iodine in an amount of about 100 mcg; iron in an amount of about 5 mg; magnesium in an amount of about 100 mg; manganese in an amount of about 2 mg; molybdenum in an amount of about 50 mcg; phosphorus in an amount of about 125 mg; potassium in an amount of about 40 mg; selenium in an amount of about 30 mcg; and zinc in an amount of about 5 mg; wherein the nutritional supplement is in one tablet.

DETAILED DESCRIPTION OF THE INVENTION

The age adjusted, targeted nutritional supplements of the present invention are particularly useful for adults 50 years and older, to not only complement daily food intake, but to support specific health benefits and to nutritionally supplement the daily diet, compensate for physiological changes and malabsorption of certain nutrients, as well as to ensure vitality, health and well being of the consumer. The nutritional supplements described herein are intended for administration to adults 50 years and older. There are presently no commercially available nutritional supplements for these older consumers that are specifically formulated to improve and/or enhance vitality, immunity, eye and bone health in a single nutritional supplement in adults 50 years and older that do not use megadose vitamin therapy.

The nutritional supplements of the present invention are designed to replenish vitamins and minerals that the body loses on a daily basis as well as compensate for physiological changes in adults 50 years and older, and to provide the body with a full range of nutrients that it needs for optimal functionality to fight disease, fatigue, tiredness and contribute to the persons overall well being. Additionally, as people get older, their metabolic function changes and declines, which in turn can affect the efficacy of micronutrient intake. The health needs of an adult over 50 years of age are very different and must be taken into account when attempting to provide nutritional supplementation. For example, as a person ages, the amount of plasma vitamin B12 decreases in part due to a decrease in gastric acidity, the presence of atrophic gastritis, food-bound vitamin B12 malabsorption, and lack of liver vitamin B12 stores. For older adults, synthetic B12 from nutritional supplements provides the more bioavailable form than that of protein-bound B12 found naturally in the diet. Aging also reduces the bioavailability of bound forms of vitamin B6, and age-related chronic illness influences vitamin B6 absorption and metabolism. The inventors have taken these nutritional and dietary differences into account when developing the nutritional formulations disclosed herein and have invented nutritional supplements uniquely age adjusted to meet the changing dietary and metabolic needs of an aging population.

These age adjusted nutritional supplements of the present invention have been uniquely formulated to address specific nutritional needs of adults over 50. More specifically, the inventors believe that specific nutritional compositions in tailored amounts may be used to improve vitality, immunity, eye and bone health and will overcome the physiological changes as well. The inventors believe that with the methods and nutritional supplements described herein, they may achieve these endpoints/effects (improved or enhanced vitality, immunity, eye and bone health) without the use of megadose vitamin therapy, which historically has been the preferred method of achieving such effects.

Megadose vitamin therapy to date has been the approach used to prevent and/or treat certain illnesses or disease states. Traditionally, megadose vitamin therapy is associated with amounts of micronutrients much greater than the RDA for such ingredients. As used herein, a megadose shall mean a dose of a micronutrient that is greater than 200% of the RDA for that micronutrient. Accordingly, it was the intent of the inventors to create nutritional supplements for use in certain indications (improved or enhanced vitality, immunity, eye and bone health) without employing megadose therapy. The nutritional supplements of the present invention are thus believed to avoid potential vitamin toxicity and other harmful side effects often associated with such megadose approaches.

Another factor the inventors had to consider when formulating nutritional compositions that contain a variety of micronutrients at amounts greater than or equal to the RDA is the ability to incorporate a sufficient amount of vitamins and/or minerals to adequately supplement the dietary intake of those ingredients without making a nutritional supplement that is too large to ingest, compress into tablets or caplets, or that would require multiple doses. Since swallowability and compliance is a particular concern for adults 50 and older, it was the intent of the inventors to provide a nutritional supplement that improves or enhances vitality, immunity, eye and bone health in a single dose.

When formulating a composition that contains micronutrients at amounts that are greater than or equal to the RDA, it can be impossible to combine these ingredients with other micronutrients, even at levels equal to or less than the RDA, because of these size and/or processing constraints. The inventors believe that the nutritional supplements of the present invention, despite having amounts of ingredients greater or equal to the RDA, can easily be formulated as tablets, capsules and other dosage forms that can easily be swallowed without needing to be administered in multiple doses. It is preferred that the nutritional supplement of the present invention is administered as one dose per day.

The RDA is the standard set of what is considered to be the proper amount of micronutrients required to be consumed by humans as part of their daily diet to ensure adequate dietary intake of such micronutrients. Every several years the RDA is reviewed, modified and updated to reflect changes in science and nutritional beliefs. As used herein, all references to RDA values cited to based upon Directives Commission Directive 2008/100/EC, which has amended Council Directive 90/496/EEC.

The majority of people do not meet the RDA of essential micronutrients through food consumption. Thus, vitamin and mineral supplementation has become a recognized method of meeting accepted medical and health standards.

The nutritional supplement for adults 50 and older may be used to improve or enhance the vitality, immunity, eye and bone health all in a single dose. As used herein, "improved vitality" and "enhanced vitality" includes improved physical strength, improved energy, reduced tiredness and sleepiness, improved transport of oxygen for energy production, enhanced physical endurance and stamina, and/or a general improvement in the sense and feeling of well-being. It is believed that the nutritional supplements of the invention may unlock energy in the human body to maintain the health and vitality of the consumer and therefore result in improving and/or enhancing the vitality of the consumer.

It is believed that folate, thiamin (vitamin B1), riboflavin (vitamin B2), niacin, vitamin B6, vitamin B12, biotin and pantothenic acid are all nutrients that can be used to support, enhance and/or improve the vitality of adults 50 years and older.

Folic acid or folate (the anionic form) also known as vitamin B9 is necessary for the production and maintenance of new cells. This is especially important during periods of rapid cell division and growth such as infancy and pregnancy. Folate is needed to synthesize DNA bases (most notably thymine, but also purine bases) needed for DNA replication. Thus folate deficiency hinders DNA synthesis and cell division, affecting most notably bone marrow and cancer, both of which participate in rapid cell division. Since folate deficiency limits cell division, erythropoisis, production of red blood cells (RBCS) is hindered and may lead to anemia. In a preferred embodiment, the amount of folic acid is about 300 mcg per day. In another preferred embodiment, folic acid is present in an amount of about 150% of the RDA.

Vitamin B1, also referred to as thiamine, is a water-soluble substance with thiazole and pyrimadine rings joined by a methylene bridge and has a biological half-life in the body of about 15 days. Thiamin is essential for neural function and carbohydrate metabolism and is dosed in the form of a pharmaceutically acceptable vitamin B1 compound. As used herein, "pharmaceutically acceptable" is a component suitable for use in humans without undue side effects, such as irritation, toxicity, and allergic response. Useful pharmaceutically acceptable vitamin B1 compounds include, but are not limited to thiamin chloride hydrochloride. In a preferred embodiment, the effective amount of vitamin B1 is about 1.6 mg per day. In an even more preferred embodiment, the effective amount of B1 is about 1.65 mg/day. In an alternative embodiment, the effective amount of B1 is about 150% of the RDA.

Vitamin B2, also referred to as riboflavin, participates in oxidation-reduction reactions in numerous metabolic pathways and in energy production via the respiratory chain. In one embodiment, the effective amount of Vitamin B2 is from about 2 mg per day; most preferably in about 2.1 mg per day. In an alternative embodiment, the effective amount of B2 is about 150% of the RDA.

Niacin is required for cell respiration, helps in the release of energy and metabolism of carbohydrates, fats, and proteins, proper circulation and healthy skin, functioning of the nervous system, and normal secretion of bile and stomach fluids. It is used in the synthesis of sex hormones, treating schizophrenia and other mental illnesses, and a memory-enhancer. Niacin given in pharmaceutical dosage improves the blood cholesterol profile, and has been used to clear the body of organic poisons, such as certain insecticides. A preferred form of niacin is niacinamide. In one embodiment, the effective amount of niacin is from about 24 mg per day. In an alternative embodiment, the effective amount of niacin is about 150% of the RDA.

Vitamin B6 or pyridoxine is involved in the production of RNA and DNA and many other biological reactions in the human body. Pyridoxal phosphate, the metabolically active form of vitamin B6, is involved in many aspects of macronutrient metabolism, neurotransmitter synthesis, histamine synthesis, hemoglobin synthesis and function and gene expression. Useful pharmaceutically acceptable vitamin B6 compounds include, but are not limited to pyridoxine, pydroxal and pyridoxamine, or salts thereof, including but not limited to pyridoxine HCL. The phosphate ester derivative pyridoxal phosphate generally serves as a coenzyme for many reactions and can help facilitate decarboxylation, transamination, racemization, elimination, replacement and beta-group interconversion reactions. An overdose of pyridoxine can cause a temporary deadening of certain nerves such as the proprioceptory nerves; causing a feeling of disembodiment common with the loss of propioception. This condition is reversible when supplementation is stopped. Accordingly, in a preferred embodiment, the effective amount of vitamin B6 is about 2 mg per day, most preferably about 2.1 mg per day. In an alternative embodiment, the effective amount of vitamin B6 is present in an amount of about 150% of the RDA.

Vitamin B12, or the cobalamins, is necessary for overall metabolism, nervous system function, metabolism of folic acid, homocysteine reduction and the production of red blood cells. There are at least three active forms of cobalamin: cyanocobalamin, hydroxocobalamin, and nitrocobalamin. Accordingly, in a preferred embodiment, the effective amount of vitamin B12 is about 3 mcg per day. In an alternative embodiment, the effective amount of vitamin B12 is present in an amount of about 120% of the RDA.

Biotin is necessary for the metabolism of carbohydrates, proteins, and fats and is needed for healthy skin and hair. In a preferred embodiment of the invention, the effective amount of biotin is about 75 mcg per day. In an alternative embodiment, the effective amount of biotin is present in an amount of about 150% of the RDA.

Pantothenic acid, also called vitamin B5, is a water-soluble vitamin required to sustain life. Pantothenic acid is needed to form coenzyme-A (CoA), and is critical in the metabolism and synthesis of carbohydrates, proteins, and fats. The derivative of pantothenic acid, pantothenol, is a more stable form of the vitamin and is often used as a source of the vitamin in multivitamin supplements. Another common supplemental form of the vitamin is calcium pantothenate. Calcium pantothenate is often used in dietary supplements because as a salt, it is more stable than pantothenic acid in the digestive tract allowing for better absorption. Megadoses of pantothenic acid between 500-1200 mg/day has been shown to reduce total serum cholesteron, LDL-cholesterol, and triglycerides, and it may increase HDL-cholesterol. Doses of 2 g/day of calcium pantothenate may reduce the duration of morning stiffness, degree of disability, and pain severity in rheumatoid arthritis patients. A preferred form of pantothenic acid is calcium pantothenate. In a preferred embodiment, the effective amount of pantothenic acid is present in an amount from about 9 mg per day. In an alternative embodiment, the effective amount of pantothenic acid is present in an amount of about 150% of the RDA.

The inventors further believe that certain combinations of key micronutrients in specific ratios and/or amounts can improve immunity by increasing the level of antioxidants that are important to regulate and strengthen the immune system and maintain the defense system of the human body. Such key micronutrients include vitamin E, vitamin C, vitamin D, iron, zinc, copper, selenium and vitamin A are all nutrients that can be used to support, enhance and/or improve the immunity of adults 50 years and older.

Key components of the immune system include the skin and mucous membranes, cilia, lysozyme, complement proteins, phagocytes, natural killer cells, t-cells and cytokines, as well as various antibodies, more specifically the five Ig isotypes. There are a multitude of factors that can affect these immune systems including but not limited to genetics, medications, surgery, diet and nutritional status, physical exercise, environmental and body temperature, environmental stress, and pollution. The inventors believe that the combination of key micronutrients (vitamin E, vitamin C, vitamin D, iron, zinc, copper, selenium and vitamin A) in the amounts disclosed herein are the optimal amounts for these micronutrients that are believed to improve or enhance the immunity of adults 50 years and older. As used herein, "enhanced immunity" and/or "improved immunity" shall include but not be limited to fewer bacterial and/or viral infections either annually or monthly; shortened or decreased time to recover from and/or reduced severity and/or fewer side effects associated with or resulting from such bacterial and/or viral infections; and an overall enhanced and/or improved quality of life. Such bacterial and/or viral infections include but are not limited to colds, influenza, respiratory, allergy and other infections caused by either bacterial and/or viral pathogens known to one skilled in the art.

Vitamin E, a fat-soluble vitamin, is an antioxidant vitamin involved in the metabolism of all cells. It protects vitamin A and essential fatty acids from oxidation in the body cells and prevents breakdown of body tissues. Vitamin E is the generic term for a group of related substances that include alpha-tocopherol, beta-tocopherol, gamma-tocopherol, and delta-tocopherol. In addition, each of these four compounds has a "d" form, which is the natural form, and a "dl" form that is the synthetic form. Preferably, in the nutritional supplement s of the present invention, vitamin E is in the natural form. In a preferred embodiment, therapeutically effective amount of vitamin E is about 18 mg per day. In an alternative embodiment, the effective amount of vitamin E is present in an amount of about 150% of the RDA.

Vitamin C, also known as ascorbic acid, is a water-soluble, antioxidant vitamin. It is important in forming collagen, a protein that gives structure to bones, cartilage, muscle, and blood vessels. Vitamin C also aids in the absorption of iron, and helps maintain capillaries, bones, and teeth. As a water-soluble antioxidant, vitamin C is in a unique position to scavenge aqueous peroxyl radicals before these destructive substances have a chance to damage lipids. It works along with vitamin E, a fat-soluble antioxidant, and the enzyme glutathione peroxidase to stop free radical chain reactions.

Vitamin C can enhance the body's resistance to an assortment of diseases, including infectious disorders and many types of cancer. It strengthens and protects the immune system by stimulating the activity of antibodies and immune system cells such as phagocytes and neutrophils. Vitamin C contributes to a variety of other biochemical functions. These include the biosynthesis of the amino acid carnitine and the catecholamines that regulate the nervous system. It also helps the body to absorb iron and to break down histamine. Although vitamin C is found in every cell, it is especially useful in key parts of the body. These include the blood, the skin, the nervous system, the teeth and bones and glands such as the thymus, adrenals and thyroid. In one embodiment, the effective amount of vitamin C is about 120 mg per day. In an alternative embodiment, the effective amount of vitamin C is present in an amount of about 150% of the RDA.

Vitamin D is a group of fat-soluble prohormones, the two major forms of which are vitamin $D_2$ (or ergocalciferol) and vitamin $D_3$ (or cholecalciferol). The term vitamin D as used herein also refers to metabolites and other analogues of these substances. Vitamin $D_3$ is produced in skin exposed to sunlight, specifically ultraviolet B radiation.

Vitamin D plays an important role in the maintenance of organ systems. It has been shown to regulate the calcium and phosphorus levels in the blood by promoting their absorption from food in the intestines, and by promoting re-absorption of calcium in the kidneys, which enables normal mineralization of bone. It is also needed for bone growth and bone remodeling. Vitamin D also has been suggested to affect the immune system by promoting phagocytosis, anti-tumor activity, and immunomodulatory functions.

Vitamin D deficiency can result from inadequate intake coupled with inadequate sunlight exposure, disorders that limit its absorption, conditions that impair conversion of vitamin D into active metabolites, such as liver or kidney disorders, or, rarely, by a number of hereditary disorders. Deficiency results in impaired bone mineralization, and leads to bone softening diseases, rickets in children and ostemalacia in adults, and possibly contributes to osteoporosis. However, sunlight exposure, to avoid deficiency, carries other risks, including skin cancer; this risk is avoided with dietary absorption, either through diet or as a dietary supplement. In one embodiment, the effective amount of vitamin D is present in an amount from about 5 mcg per day and is present as vitamin D3. In an alternative embodiment, the effective amount of vitamin D3 is present in an amount of about 100% of the RDA.

Iron is used in the production of hemoglobin and myoglobin. In the nutritional supplement described herein, the iron is doesed in the form of a pharmaceutically acceptable iron compond, which as used herein means a compound that is suitable for use in humans without undue side effects, such as irritation, toxicity and allergic resonse. Examples include, but are not limited to ferrous fumarate, ferrous sulfate, carbonyl iron, ferrous gluconate, ferrous chloride, ferrous lactate, ferrous tartrate, ferrous succinate, ferrous glutamate, ferrous citrate, ferrous phyrophospate, ferrous cholinisocitrate, ferrous carbonate, iron-sugar-carboxylate complexes and combinations thereof. The preferred form of iron is ferrous fumarate. In one embodiment, the effective amount of iron is present in an amount of about 2 mg per day, more preferably 2.1 mg per day. In an alternative embodiment, the effective amount of iron is present in an amount of about 15% of the RDA.

Zinc is an essential mineral that is naturally present in some foods, added to others, and available as a dietary supplement. Zinc is involved in numerous aspects of cellular metabolism. It is required for the catalytic activity of approximately 100 enzymes and it plays a role in immune function, protein synthesis, wound healing, DNA synthesis and cell division. A daily intake of zinc is required to maintain a steady state because the body has no specialized zinc storage system. Zinc deficiency is characterized by growth retardation, loss of appetite, and impaired immune function. In more severe cases, zinc deficiency causes hair loss, diarrhea, delayed sexual maturation, impotence, hypogonadism in males, and eye and skin lesions. Weight loss, delayed healing of wounds, taste abnormalities, and mental lethargy can also occur.

Severe zinc deficiency may also depresses immune function, and even mild to moderate degrees of zinc deficiency can impair macrophage and neutrophil functions, natural killer cell activity, and complement activity. The body requires zinc to develop and activate T-lymphocytes. Individuals with low zinc levels have shown reduced lymphocyte proliferation response to mitogens and other adverse alterations in immunity that can be corrected by zinc supplementation. These alterations in immune function might explain why low zinc status has been associated with increased susceptibility to pneumonia and other infections.

Several forms of zinc, including zinc gluconate, zinc sulfate, zinc oxide and zinc acetate may be used in the nutritional supplements described herein. The percentage of elemental zinc varies by form. For example, approximately 23% of zinc sulfate consists of elemental zinc; thus, 220 mg of zinc sulfate contains 50 mg of elemental zinc. The preferred form of zinc is zinc oxide. In one embodiment, the effective amount of zinc is present in an amount of about 5 mg per day. In an alternative embodiment, the effective amount of zinc is present in an amount of about 50% of the RDA.

Copper, an essential trace mineral, is important for the function of two very important enzymes in our bodies. The first is superoxide dismutase (SOD), which is one of the most powerful free-radical fighters available in humans. In this way, copper supports immune systems and our ability to fight disease.

Copper is also necessary for iron utilization, which is required for energy. If copper levels are low and iron is inhibited, fatigue and muscle weakness can follow. By supporting iron, copper also ensures healthy respiratory function, delivering oxygen to red blood cells. In addition, our bodies need copper to produce adenosine triphosphate (ATP), which is a key energy producer in humans. In the nutritional supplement described herein, the copper is administered in a pharmaceutically acceptable form including but not limited to cupric oxide, cupric citrate, cupric sulfate, cupric carbonate, cupric gluconate and combinations thereof. In a preferred embodiment the copper is present in the amount of about 0.5 mg per day. In an alternative embodiment the copper is present in an amount of about 50% of the RDA.

Selenium is an essential trace element that functions as a component of enzymes involved in antioxidant protection and thyroid hormone metabolism. Selenium possesses antioxidant properties, and has been shown to reduce the risk of heart attack and heart disease. Characteristic signs of selenium deficiency have not been described in humans, but very low selenium status is a factor in the etiologies of a juvenile cardiomyopathy (Keshan Disease) and a chondrodystrophy (Kashin-Beck Disease) that occur in selenium-deficient regions of China. In one embodiment, the effective amount of selenium is present in an amount of about 30 mcg per day. In an alternative embodiment, the effective amount of selenium is present in an amount of about 55% of the RDA.

Vitamin A, a bi-polar molecule formed with bi-polar covalent bonds between carbon and hydrogen, is linked to a family of similarly shaped molecules, the retinoids. Its important part is the retinyl group, which can be found in several forms. Vitamin A can be found as an ester, primarily retinyl palmitate (found in foods and converted to retinol in the small intestine. Vitamin A can also exist also as retinal or as retinoic acid. Precursors to the vitamin are present in foods of plant origin as some of the members of the carotenoid family of compounds. Common provitamin A carotenoids found in foods that come from plants are betacarotene, alpha carotene and betacryptoxanthin. Among these, beta-carotene is most efficiently made into retinol. Alpha carotene and betacryptoxanthin are also converted to vitamin A, but only half as efficiently as betacarotene.

Vitamin A plays a role in a variety of functions throughout the body, such as: vision, gene transcription, immune function, embryonic development and reproduction, bone metabolism, haematopoiesis, skin health, reducing risk of heart disease, and antioxidant activity. Vitamin A deficiency can occur as either a primary or secondary deficiency. A primary vitamin A deficiency occurs among children and adults who do not consume an adequate intake of yellow and green vegetables, fruits and liver. Secondary vitamin A deficiency is associated with chronic malabsorption of lipids, impaired bile production and release, low fat diets, and chronic exposure to oxidants, such as cigarette smoke. Vitamin A is a fat soluble vitamin and depends on micellar solubilization for dispersion into the small intestine, which results in poor utilization of vitamin A from low-fat diets. Zinc deficiency can also impair absorption, transport, and metabolism of vitamin A because it is essential for the synthesis of the vitamin A transport proteins and the oxidation of retinol to retinal.

In a preferred embodiment, vitamin A ratio of retinol (in the form of vitamin A acetate) and betacarotene is 50:50. In an even more preferred embodiment, the total amount of vitamin A (retinol+betacarotene) is about 800 mcg per day. In an alternative embodiment, the total amount of vitamin A present in the nutritional supplement is about 100% of the RDA.

The nutritional supplement for adults 50 years and older is also specially balanced nutrient combinations with higher levels of key nutrients and in the amounts and ratios described herein may help to support eye health. The inventors believe that the nutrient combination of lutein, vitamin A, riboflavin (vitamin B2) and vitamin E in the amounts described herein can help to support and/or improve eye health in an adult over 50 years of age.

Lutein, a naturally occurring carotenoid, was found to be concentrated in the macula, a small area of the retina responsible for central vision. The hypothesis for the natural concentration is that lutein helps protect from oxidative stress and high-energy light. Various research studies have shown that a direct relationship exists between lutein intake and pigmentation in the eye. Lutein is also believed to play a role in increasing the macula pigmentation and therefore decreases the risk for eye diseases such as Age-related Macular Degeneration (AMD). In a preferred embodiment, the effective amount of lutein is about 1000 mcg per day.

The nutritional supplement for adults 50 years and older is also specially balanced nutrient combinations with higher levels of key nutrients and in the amounts and ratios described herein may help to support bone health. The inventors believe that the nutrient combination of calcium, vitamin K and vitamin D in the amounts described herein can help to support bone health in adults over 50 years of age.

Calcium is an important component of a health diet and is a mineral that is necessary for life. The National Osteoporosis Foundation says, "Calcium plays an important role in building stronger, denser bones early in life and keeping bones strong and healthy later in life." Approximately ninety-nine percent of the body's calcium is stored in the bones and teeth. Long-term calcium deficiency can lead to rickets and poor blood clotting and in case of a menopausal woman, it can lead to osteoporosis. While a lifelong deficit can affect bone and tooth formation, over-retention can cause hypercalcemia (elevated levels of calcium in the blood), impaired kidney function and decreased absorption of other minerals. Pharmaceutically acceptable sources of calcium compounds include but is not limited to calcium carbonate, dibasic calcium phosphate, tribasic calcium phosphate, calcium gluconate, calcium lactate, calcium citrate and combinations thereof. In a preferred embodiment, the calcium is present in an amount of about 162 mg per day. In an alternative embodiment, the calcium is provided in an amount of 20 percent of the RDA.

Vitamin K denotes a group of lipophilic, hydrophobic vitamins that are need for postranslational modification of certain proteins. Chemically they are 2-methyl-1,4-napthoquinone derivatives. All members of the vitamin K group of vitamins share a methylated napthoquinone ring structure, and vary in the aliphatic side chain attached at the 3-position. Phylloquinone (also known as vitamin $K_1$) invariably contains in its side chain four isoprenoid residues, one of which is unsaturated.

It is generally accepted that the naphthoquinone is the functional group, so that the mechanism of action is similar for all K-vitamins. Substantial differences may be expected, however, with respect to intestinal absorption, transport, tissue distribution, and bio-availability. These differences are caused by the different lipophilicity of the various side chains, and by the different food matrices in which they occur. Vitamin K deficiency is very rare. It occurs when the body can't properly absorb the vitamin from the intestinal tract. Vitamin K deficiency can also occur after long-term treatment with antibiotics. Individuals with vitamin K deficiency are usually more likely to have bruising and bleeding. Vitamin K is an active blood clotting agent and assist in bone formation. Preferably, vitamin K is in the form of vitamin K1 and is in an amount of about 30 mcg per day. In an alternative embodiment, the vitamin K1 is present in an amount of about 40% of the RDA.

In order to provide a nutritional supplement for adults over 50 that not only for improving and/or enhancing vitality, immunity, eye and bone health, additional micronutrients are also incorporated. The benefit of having one dose of all the vitamins and minerals in the right ratio and amounts of nutrients that are beneficial for vitality, immunity, eye and bone health, but also for dietary nutritional supplementation is that it ensures a higher compliance rate. Rather than having to take multiple supplements, pills, tablets or other dosage forms, adults 50 and older can take 1 dose and receive the vitamins and minerals and micronutrients for daily dietary supplementation. For example, additional micronutrients include but not limited to phosphorus, chloride, chromium, iodine, magnesium, manganese, molybdenum, and potassium.

Phosphorus is needed for bone development and is a constituent in all major classes of biochemical compounds. Phosphorous, in the form of phosphate in adenosine triphosphate is a key energy source required for most metabolic processes. Pharmaceutically acceptable phosphorus compounds include, but are not limited to, forms of calcium phosphate, sodium phosphate, potassium phosphate, ammonium phophate, glycerol phosphate, and combinations thereof. In a preferred embodiment, the amount of phosphorus is about 125 mg. In an alternative embodiment, the phosphorus is about 18% of the RDA.

Chloride is needed to help maintain the ionic and fluid balance in the body, and is an essential component of gastric and intestinal secretions. Useful pharmaceutically acceptable chloride compounds include, but are not limited to, sodium chloride, chromium chloride, stannous chloride and potassium chloride. In a preferred embodiment, the amount of chloride is about 36 mg; in an even more preferred embodiment the chloride is about 36.3 mg. In an alternative embodiment, the chloride is about 5% of the RDA.

Chromium assists in the regulation of glucose metabolism, is used in the synthesis of fatty acids and cholesterol, assists in transporting proteins, lowers LDL blood levels, and raises high density lipoproteins blood levels. In the nutritional supplement, chromium is dosed in a pharmaceutically acceptable chromium compound. Useful pharmaceutically acceptable chromium compounds include, but are not limited to, chromium chloride, yeast-bound chromium, picolinate, niacin-bound chromium, and combinations thereof. In a preferred embodiment, the chromium is present in an amount of about 40 mcg. In an alternative embodiment, the chromium is about 100% of the RDA.

Iodine helps to metabolize fats and is necessary for proper thyroid function and helps to reduce fibrocystic breast conditions. In the nutritional supplement of the present invention, the iodine is administered in a pharmaceutically acceptable form of iodine, including but not limited to potassium iodide, sodium iodide and combinations thereof. In a preferred embodiment, the iodine is in the form of potassium iodide. In yet another embodiment, the amount of iodine in the nutritional supplement is about 100 mcg. In an alternative embodiment, the iodine is about 67% of the RDA.

Magnesium is used in bone formation and growth, prevents bone loss, relaxes coronary arteries, is used in managing pre-eclampsia, treating cardiac arrhythmias, and managing diabetes. In the nutritional supplement, magnesium is dosed in the form of a pharmaceutically acceptable magnesium compound. Useful pharmaceutically acceptable magnesium compounds include, but are not limited to, magnesium stearate, magnesium carbonate, magnesium oxide, magnesium hydroxide, magnesium sulfate, and combinations thereof. In a preferred embodiment, the magnesium is present in an amount of about 100 mg. In an alternative embodiment, the magnesium is about 27% of the RDA.

Molybdenum may facilitate proper metabolism of fats, carbohydrate and iron and may protect against certain cancers. Pharmaceutically acceptable molybdenum compounds include, but are not limited to, sodium molybdate, molybdenum amino acid chelates, and combinations thereof. In a preferred embodiment, the molybdenum is present in an amount of about 50 mcg. In an alternative embodiment, the molybdenum is about 100% of the RDA.

Potassium is needed to regulate water balance, levels of acidity, blood pressure and neuromuscular function. Potassium is also required for carbohydrate and protein metabolism. In the nutritional supplement, potassium is dosed in the form of a pharmaceutically acceptable potassium compound. Useful pharmaceutically acceptable potassium compounds include, but are not limited to, potassium chloride, potassium sulfate; potassium glycerophosphate, potassium citrate, potassium gluconate, potassium phosphate, and combinations thereof. In a preferred embodiment, the potassium is present in an amount of about 40 mg. In an alternative embodiment, the potassium is about 2% of the RDA.

A low level of manganese in the body may be associated with diabetes. Accordingly manganese appears to have a role in the control of blood sugar levels. Manganese may also have a role in the metabolism of amino acids and certain vitamins. Pharmaceutically acceptable manganese compounds include, but are not limited to, manganese chloride, manganese sulfate, and combinations thereof. In a preferred embodiment, the manganese is present in an amount of about 2 mg. In an alternative embodiment, the manganese is about 100% of the RDA.

The nutritional supplement is to be administered in a single unit dosage form. As used herein, single unit dosage form shall mean a dosage form wherein all the micronutrients of the composition are in a single pill, tablet, caplet, capsule, chewable tablet, quick dissolve tablet, effervescent tablet, hard gelatin capsule, soft gelatin capsule, powder, liquid suspension, and food product. It however is recognized that the single unit dosage form may be administered as a single dose, i.e. take 1 pill per day; or in multiple doses. Preferably the dosage form is administered as 1 dose per day.

The nutritional supplements and compositions described herein can be made in a variety of forms, such as the following pharmaceutical compositions: a pill, a tablet, a caplet, a capsule, a chewable tablet, a quick dissolve tablet, an effervescent tablet, a hard gelatin capsule, a soft gelatin capsule, a powder, a liquid suspension, and a food product. One skilled in the art would recognize there are also other viable ways for delivering the nutritional supplement to a user. In a preferred embodiment, the nutritional supplement is in a solid dosage form; in an even more preferred embodiment, the solid dosage form is a tablet.

Furthermore, these compositions can be made using conventional equipment and techniques known in the art. When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbents, such as silicon dioxide; preservatives, such as methylparaben, propylparaben, and sodium benzoate; surfactants, such as sodium lauryl sulfate, polysorbate 80, and the like; and colorants, such as F.D. & C dyes and the like. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

Furthermore, in addition to the inactive ingredients described herein, the compositions preferably comprise additional micronutrients to supplement the daily dietary intake of those micronutrients.

While the invention has been described with respect to certain specific embodiments, it will be appreciated that many modifications and changes may be made by those skilled in the art without departing from the invention. It is intended, therefore, by the appended claims to cover all such modifications and changes as may fall within the true spirit and scope of the invention.

EXAMPLES

Example 1

| Nutrient | Unit | Amount | % RDA |
|---|---|---|---|
| Total A | Mcg | 800 | 100 |
| Vitamin A (retinol) | Mcg | 400 | |
| Beta-Carotene | Mg | 2.4 | |
| Thiamine (B1) | Mg | 1.65 | 150 |
| Riboflavin (B2) | Mg | 2.1 | 150 |
| Niacin | Mg | 24 | 150 |
| Vit B6 | Mg | 2.1 | 150 |
| Vit B12 | Mcg | 3 | 120 |

-continued

| Nutrient | Unit | Amount | % RDA |
|---|---|---|---|
| Vitamin C | Mg | 120 | 150 |
| Vit D3 | Mcg | 5 | 100 |
| Vitamin E | Mg | 18 | 150 |
| Vitamin K1 | Mcg | 30 | 40 |
| Biotin | Mcg | 75 | 150 |
| Folic Acid | Mcg | 300 | 150 |
| Pantothenic Acid | Mg | 9 | 150 |
| Calcium | Mg | 162 | 20 |
| Phosphorus | Mg | 125 | 18 |
| Chloride | Mg | 36.3 | 5 |
| Chromium | Mcg | 40 | 100 |
| Copper Sulfate | Mg | 0.5 | 50 |
| Iodine | Mcg | 100 | 67 |
| Iron | Mg | 2.1 | 15 |
| Magnesium | Mg | 100 | 27 |
| Manganese | Mg | 2 | 100 |
| Molybdenum | Mcg | 50 | 100 |
| Potassium | Mg | 40 | 2 |
| Selenium | Mcg | 30 | 55 |
| Zinc | Mg | 5 | 50 |
| Lutein | Mcg | 1000 | |

The invention claimed is:

1. A nutritional supplement for providing nutritional support for improved vitality, improved immunity, eye and bone health in a human subject fifty years of age and older consisting of: vitamin A in an amount of about 800 mcg; vitamin B1 in an amount of about 1.4 mg; vitamin B2 in an amount of about 1.75 mg; niacin in an amount of about 20 mg; vitamin B6 in an amount of about 2 mg; vitamin B12 in the form of cyanocobalamin in an amount of about 2.5 mcg; vitamin C in an amount of about 100 mg; vitamin D in an amount of about 5 mcg; vitamin E in the dl form in an amount of about 15 mg; vitamin K in an amount of about 30 mcg; biotin in an amount of about 62.5 mcg; folic acid in an amount of about 200 mcg; pantothenic acid in the form of calcium pantothenate in an amount of about 7.5 mg; calcium in an amount of about 162 mg; chloride in an amount of about 36.3 mg; chromium in an amount of about 40 mcg; copper in an amount of about 0.5 mg; iodine in an amount of about 100 mcg; iron in an amount of about 5 mg; magnesium in an amount of about 100 mg; manganese in an amount of about 2 mg; molybdenum in an amount of about 50 mcg; phosphorus in an amount of about 125 mg; potassium in an amount of about 40 mg; selenium in an amount of about 30 mcg; zinc in an amount of about 5 mg; and at least one excipient selected from the group consisting of gelatin, pregelatinized starch, hydrogenated vegetable oil, stearic acid, lactose, mannose, sucrose, carboxymethylcellulose, sodium starch glycolate, povidone, polyvinylalcohol, silicon dioxide, methylparaben, propylparaben, sodium benzoate, sodium laurel sulfate, polysorbate 80, and FD&C dyes; wherein the nutritional supplement is in one tablet and wherein, after administration, the nutritional supplement provides nutritional support for improved vitality, improved immunity, eye and bone health in a human subject fifty years of age and older.

* * * * *